US00PP36936P2

(12) United States Plant Patent
Hansen

(10) Patent No.: US PP36,936 P2
(45) Date of Patent: Sep. 2, 2025

(54) ***CAMPANULA* PLANT NAMED 'Bells and Whistles'**

(50) Latin Name: ***Campanula glomerata* L.**
Varietal Denomination: Bells and Whistles

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,340

(22) Filed: Nov. 22, 2024

(51) Int. Cl.
*A01H 5/02* (2018.01)
*A01H 6/26* (2018.01)

(52) U.S. Cl.
USPC ..... Plt./157

(58) Field of Classification Search
USPC ..... Plt./414
See application file for complete search history.

(56) References Cited

U.S. PATENT DOCUMENTS

PP22,738 P2 * 5/2012 Blom ..... A01H 5/02
Plt./414

OTHER PUBLICATIONS https://www.etsy.com/shop/MrPerennial?ref=shop-header-name&listing_id=1669129171&from_page=listing) (Year: 2024).*

* cited by examiner

*Primary Examiner* — Shubo (Joe) Zhou
*Assistant Examiner* — Zachariah Allan Kay

(57) ABSTRACT

The new and distinct Bellflower plant, *Campanula* plant named 'Bells and Whistles' with dense mounded habit, dark-green lanceolate foliage and numerous dark violet-blue campanulate flowers over a six week period clustered at nodes and ends of upright heavily branched stems beginning in late June.

2 Drawing Sheets

Botanical designation: *Campanula glomerata* L.
Cultivar denomination: 'Bells and Whistles'.

STATEMENT REGARDING PRIOR DISCLOSURES UNDER 37 CFR 1.77 (b) (6)

The first disclosure and offer for sale of the claimed plant was on Dec. 1, 2023, when the claimed plant was displayed as a photograph with a brief description in a website maintained by Walters Gardens, Inc. Subsequently, the new plant was advertised in the "Walters Gardens 2024-2025 Catalog" first distributed on May 23, 2024. Walters Gardens, Inc. obtained the new plant and all information about the new plant from the inventor. No plants of *Campanula* 'Bells and Whistles' have been sold in this country or anywhere in the world nor has any disclosure of the new plant been made more than one year prior to the filing date of this application, and such disclosure within one year was either derived directly or indirectly from the inventor.

BACKGROUND OF THE PLANT

The present invention relates to the new and distinct clustered bellflower herein also referred to as *Campanula* 'Bells and Whistles', by the cultivar name, 'Bells and Whistles', or as the "new plant." The new plant was derived from seed collected on Oct. 8, 2014, from a plant in an isolation block, in a research facility in Zeeland, Michigan, that was an unreleased, proprietary, selection identified only by the breeder code "Lavender" (not patented). The male parent was a sibling of "Lavender" (not patented). The single seedling represented by 'Bells and Whistles' was selected from a group of seedlings by the inventor, isolated and compared in subsequent years to other *Campanula* and subsequently found to be different from all cultivars known to the discoverer and eventually given the breeder code 14-1-11.

Asexual propagation at the same nursery in Zeeland, MI, USA by division and later by basal cuttings and shoot tip tissue culture have all shown 'Bells and Whistles' to be stable and reproduce true to type in successive generations since late June 2019.

SUMMARY OF THE PLANT

*Campanula* 'Bells and Whistles' has not been observed in all possible environmental conditions. The phenotype may vary slightly with changes in environments such as light intensity, fertility, water availability, etc. without, however, any variation in genotype.

*Campanula* 'Bells and Whistles' is distinct from all cultivars known to the inventor in the following traits:

1. Narrow, serrulate, dark-green foliage forming a dense mounded habit;
2. Upright stems are heavily-branched with dark violet-blue bell-shaped flowers clustered at the nodes and ends;
3. Long flowering period beginning in late-June and continuing for about six weeks.

Plants of *Campanula* 'Bells and Whistles' are most similar to 'Allgentibl' U.S. Plant Pat. No. 24,687 'Freya' U.S. Plant Pat. No. 22,738, 'Allgentitwist' U.S. Plant Pat. No. 25,403, and 'Church Bells' U.S. Plant Pat. No. 32,290.

'Allgentibl' is shorter in habit and produces fewer flowers over a shorter period of time. 'Freya' has a slightly more compact habit in both height and width and the flowers are more lavender-purple 'Allgentitwist' has a shorter habit with white sepals and lighter purple petals. 'Church Bells' has a much shorter habit, flowers that are a lighter violet-purple with a broader apex, starting about one to two weeks earlier with flowering over a longer period.

The female parent, "Lavender," is taller and more open in habit and has lighter colored flowers. The male parent has a taller and more open in habit and has lighter colored flowers.

BRIEF DESCRIPTION OF THE DRAWINGS

The color drawings illustrate the overall characteristics of *Campanula* 'Church Bells' as a four-year-old plant. The colors are as true as reasonably possible given the technology available. The color values may vary slightly depending on light intensity and quality.

DETAILED BOTANICAL DESCRIPTION

Figure 1:
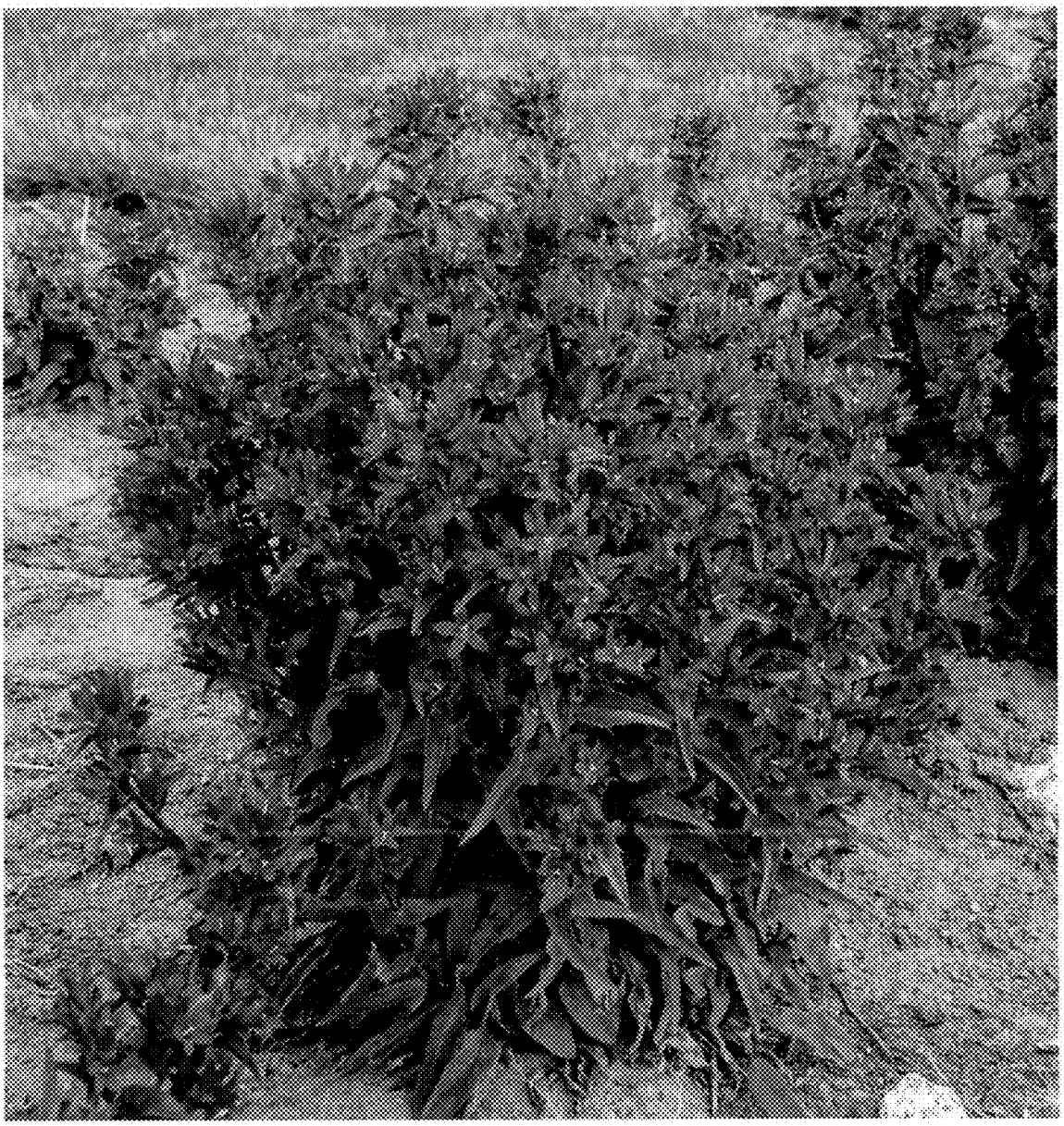
FIG. 1 shows the new plant in a landscape environment in peak flower.
Figure 2:
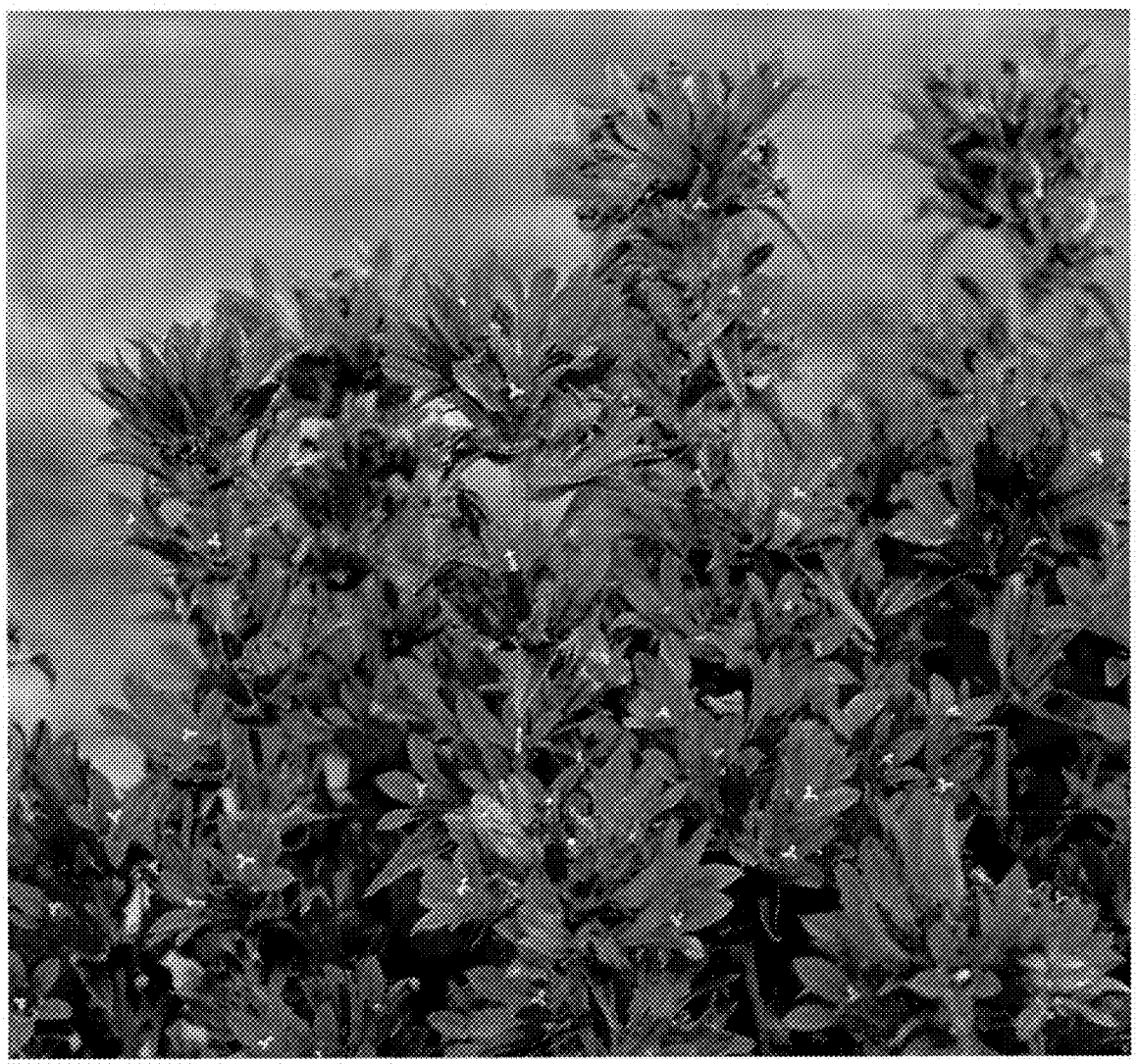
FIG. 2 shows a close-up of the flowers and buds of the new plant.

The following description is based on a two-year-old plant growing in a full-sun display garden in Zeeland, MI, USA. Environmental conditions for the growing season daytime temperatures range between 12° C. to 35° C., and night temperatures range between 6° C. to 24° C. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent "Lavender"; male or pollen parent sibling to "Lavender";

Asexual propagation: Cuttings, about 12 to 20 days to initiate roots; time to finish in a 3.8-liter container about 7 months flowering a vernalization period of 15 weeks;

Roots: Thin, fibrous, and highly branching; color between RHS 158D and RHS 162D;

Plant habit: Up-right, rounded, herbaceous, winter-hardy, perennial mound; with heavily branched flower stems up to 71 cm tall; average about 65 cm tall and about 64 cm across;

Leaves: Alternate to dextrose; upper cauline sessile; simple; lanceolate; adaxial and abaxial puberulent to hirsutulous; adaxial slightly lustrous and slightly rugose; abaxial surface matte; acute apex; attenuate to cordate base; margin serrulate and micro-ciliolate;

Leaf size: To 14.5 cm long and 4.4 cm wide, average about 10 cm long and 3.2 cm wide;

Leaf color: Young expanding leaves adaxial nearest RHS 138A and abaxial nearest RHS 138A; mature leaves adaxial between RHS 137A and RHS 137B, abaxial between RHS 147C and RHS 147B;

Veins: Reticulate; glabrous adaxial, puberulent abaxial;

Vein color: Adaxial midrib and main veins nearest RHS 145A and secondary veins nearest RHS 137A, abaxial midrib nearest RHS 145C and secondary veins nearest RHS 147B;

Petiole: On basal leaves and lower cauline leaves only; concavo-convex; clasping base; puberulent adaxial and abaxial; margin ciliolate;

Petiole size: To about 6 cm long and 2.5 mm across; becoming sessile on distal cauline leaves;

Petiole color: adaxial and abaxial margin nearest RHS 146B; adaxial center between RHS 146D and RHS 145A; abaxial center nearest RHS 146D;

Flower: Single; perfect; actinomorphic; campanulate; protandrous; on terminal branches; about 35 mm long and about 25 mm across at apex; attitude outright to slightly upright;

Flower fragrance: Not detected;

Flowering period: Beginning late June for about 6 weeks; up to 70 flowers per branched peduncle, and 50 flowers per average branched peduncle; about 1,300 flowers per plant;

Flower longevity: 5 to 7 days;

Flower buds: One day prior to opening-oblong ellipsoidal; rounded apiculate apex and rounded base; about 23 mm long and 5 mm diameter; heavily fluted longitudinally;

Flower bud color: One day prior to opening-basal 5 mm of corolla nearest RHS 155C, distally between RHS 86A and RHS 86B;

Petals: Typically five in a single whorl; lanceolate; acute apex; basal 16 mm fused, free and flared in distal 12 mm; margin entire; pubescent in adaxial basal two-thirds and glabrous in distal one-third portion, glabrous abaxial; about 27 mm long and 6 mm wide above fusion;

Petal color: Adaxial between RHS 90B and RHS N88B, adaxial basal 3 mm nearest RHS NN155C; abaxial basal 3 mm nearest RHS NN155C, with middle and distal portion between RHS 90B and RHS N88B; no spots are present either adaxial or abaxial; no change in flower color from opening to maturity;

Corolla: Single; to about 35 mm long and 26 mm across; fused in basal 16 mm; fused portion to about 10 mm diameter distally and 4 mm diameter at base; lobes slightly angled outward from central axis;

Androecium: Typically five;

*Filament*.—connate in the basal 2 mm and about 1.5 to 2 mm across, distally cylindrical, about 2 to 2.5 mm long and about 0.2 to about 0.3 mm diameter in the distal 2 mm; color nearest RHS NN155C.

*Anther*.—very oblong; basifixed; longitudinal; about 5 mm long and 1 mm across; color nearest RHS 18C.

*Pollen*.—abundant; color nearest RHS 11D.

Gynoecium: Single; half-inferior; about 15 mm long;

*Style*.—cylindrical; about 12 mm long and 0.7 mm diameter; color between RHS 92D and RHS NN155C.

*Stigma*.—bifid to trifid; decurrent; to about 7 mm long and 0.5 mm diameter; color nearest RHS NN155B.

*Ovary*.—obconical; about 4 mm tall and 4 mm diameter at apex; nearest RHS NN155A.

Calyx: Campanulate; to about 11 mm long and 16 mm wide at apex;

Sepals: Five; linear; narrowly acute apex; fused in the basal 5 mm forming hypanthium; margin serrulate and ciliate; glabrous adaxial and abaxial; about 10 mm long above hypanthium, about 3.5 mm wide above fusion;

Sepal color: Adaxial and abaxial nearest RHS 138A above hypanthium and nearest RHS 145C proximally at hypanthium;

Inflorescence: Panicle with flowers arranged in terminal and axillary clusters; flowering in upper 24 cm and 8.5 cm wide;

Stem: 8 nodes below flowering branches; to 9 mm diameter at base; terete; fistulous; sparsely pubescent;

Peduncle: About 26 per plant; terete; carinate with longitudinal angular ridges along sides of leaf attachment; sparsely pubescent; upright attitude; strong; stiff; to about 9 mm diameter at base and 71 cm long; about fifteen branching nodes, average internode spacing about 4.5 cm; branches to about 19 cm long and 4 mm diameter at base;

Peduncle branches: Heavily-branched with about ten branches; to about 22 cm long and 2.5 mm diameter at base; branch angle to about 60° above horizontal;

Peduncle and branch color: Between RHS 143A and RHS 141A at carina, nearest RHS 146D between carina, and in high light exposure carina and portion between carina nearest RHS 187B;

Pedicel: Cylindrical; glaucous; thin, wiry, strong; about 1 to 2 mm long and 1 mm diameter;

Pedicel color: Between RHS 145A and RHS 146D;

Seed: Slightly flattened ellipsoidal; rounded apex and base; surface glabrous; about 1 mm long and 0.7 mm across center;

Seed color: Variable, some seeds between RHS 165A and RHS 165B;

*Campanula* 'Bells and Whistles' is tolerant of winter temperatures from USDA hardiness at least to zones 3 to 8. The new plant grows best with good drainage and adequate moisture. It is not known to be tolerant of diseases and pest that are common to other *Campanula* cultivars.

I claim:

1. The new and distinct cultivar of *Campanula* plant named 'Bells and Whistles' as described and illustrated.

* * * * *